United States Patent [19]

Thies et al.

[11] Patent Number: 5,441,878

[45] Date of Patent: Aug. 15, 1995

[54] PREPARATION OF UNIFORM DROPLETS BY USING GAS PRESSURE TO FORCE LIQUID FROM A SYRINGE AND FLOWING GAS TO DETACH DROPLETS

[75] Inventors: Curt Thies, Ballwin, Mo.; Andrew Stanisz, Dundas, Canada

[73] Assignee: Thies Technology, Inc., Ballwin, Mo.

[21] Appl. No.: 130,353

[22] Filed: Dec. 8, 1987

[51] Int. Cl.⁶ .................. C12N 11/10; C12N 11/04; C12M 1/40; B29B 9/00

[52] U.S. Cl. ........................... 435/178; 264/5; 264/14; 435/182; 435/240.22; 435/240.4; 435/288

[58] Field of Search .............. 435/174, 176, 177, 180, 435/182, 288; 264/12, 13, 14, 5

[56] References Cited

U.S. PATENT DOCUMENTS

| | | | |
|---|---|---|---|
| 2,800,457 | 7/1957 | Green et al. | 252/316 |
| 4,251,387 | 2/1981 | Lim et al. | 252/316 |
| 4,255,411 | 3/1981 | Lim et al. | 424/1 |
| 4,257,884 | 3/1981 | Lim | 210/456 |
| 4,311,690 | 1/1982 | Buehler et al. | 424/1 |
| 4,322,311 | 3/1982 | Lim et al. | 252/316 |
| 4,324,683 | 4/1982 | Lim et al. | 252/316 |
| 4,352,883 | 10/1982 | Lim et al. | 435/178 |
| 4,389,419 | 6/1983 | Lim et al. | 426/72 |
| 4,391,909 | 7/1983 | Lim | 435/178 |
| 4,407,957 | 10/1983 | Lim | 435/178 |
| 4,409,331 | 10/1983 | Lim | 435/178 |
| 4,415,512 | 11/1983 | Torobin | 264/13 X |
| 4,464,317 | 8/1984 | Thies et al. | 264/4.3 |
| 4,495,288 | 1/1985 | Jarvis, Jr. et al. | 435/241 |
| 4,692,284 | 9/1987 | Braden | 264/4.3 |

OTHER PUBLICATIONS

Madan et al., (1978) J. Pharm. Sci. 67:409–411.
Nakano et al., (1979) J. Pharm. Pharmacol. 31:869–872.
Madan et al., (1978) J. Pharm. Pharmacol. 30:65–67.
Thies, (1987) "Encyclopedia of the Polymer Science and Engineering," 2nd. ed. (1987) 9:724–745 (John Wiley & Sons).
Salib et al., (1978) Pharm. Ind. 40:1230–1234.

Primary Examiner—David M. Naff
Attorney, Agent, or Firm—Fish & Richardson

[57] ABSTRACT

An apparatus and method for the formation of droplets of uniform size on a laboratory scale are described. A syringe having a plunger and a needle with an orifice at the tip corresponding to a 12–30 gauge needle is inserted into a block member having a cavity such that the needle of the syringe extends through an opening in the bottom of the block member. The block member has a gas inlet into a side of the cavity for flowing of gas pass the orifice of the needle. The block member is mounted in a support housing such that the syringe is in a vertical position. To form droplets, pressure is applied to the plunger, preferably by a piston under gas pressure, to force liquid from the needle tip orifice to form droplets and flowing gas pass the tip to detach droplets of a desired size. In a preferred embodiment, the liquid is a suspension containing living cells and alginate, and droplets formed are solidified in a solidifying medium such as a calcium chloride solution to obtain microcapsules containing living cells.

7 Claims, 3 Drawing Sheets

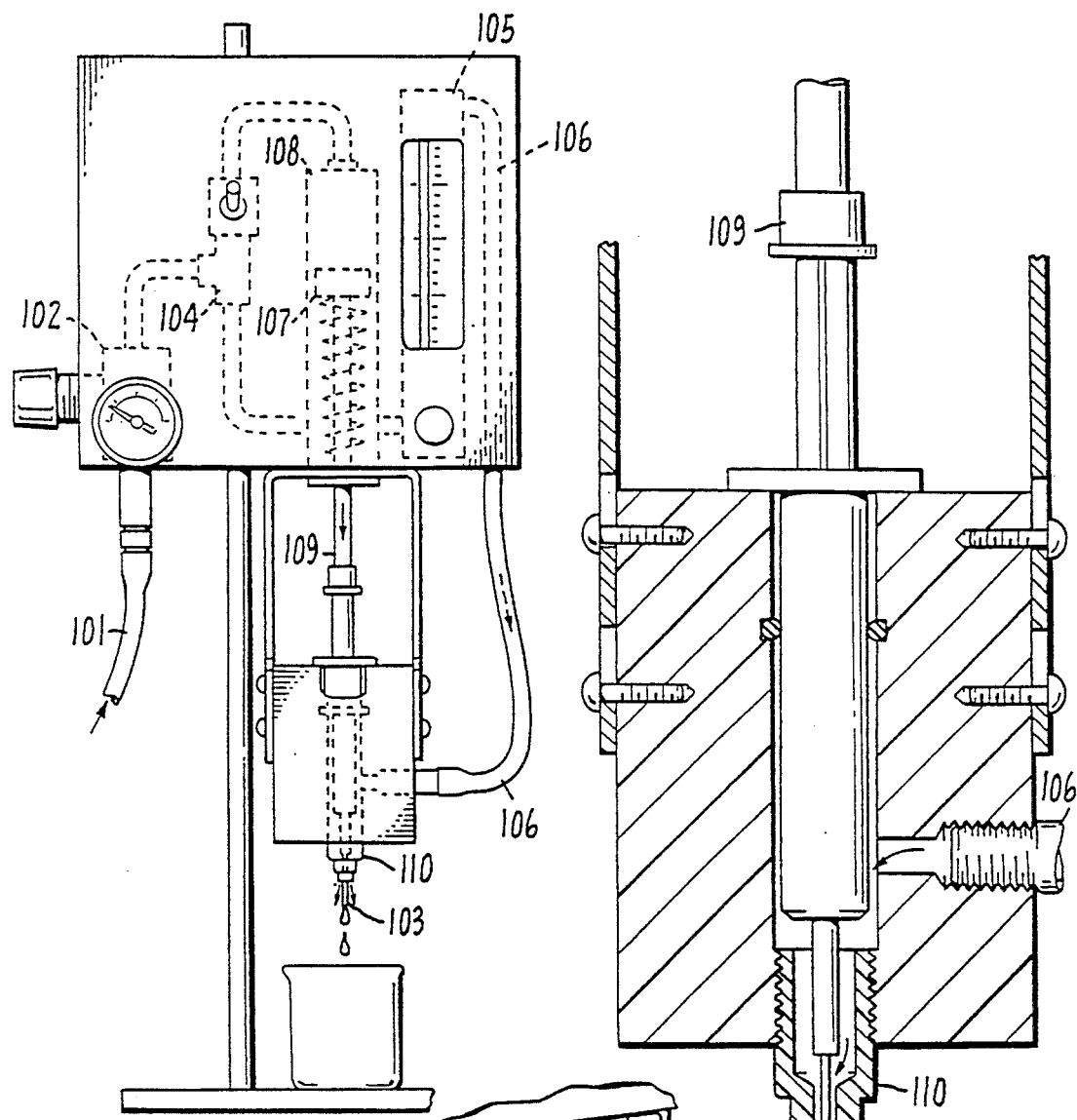
FIG. 1.
FIG. 2.
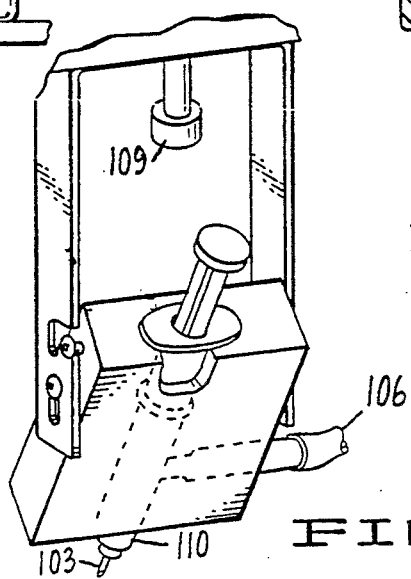
FIG. 3.

PREPARATION OF UNIFORM DROPLETS BY USING GAS PRESSURE TO FORCE LIQUID FROM A SYRINGE AND FLOWING GAS TO DETACH DROPLETS

TECHNICAL FIELD

The invention relates to the field of particle formation and microencapsulation. In particular, it concerns a method to obtain uniform droplets for formation of gelled or solid particulates.

BACKGROUND ART

Particles, beads and microcapsules have many uses in many areas of technology. The formation of particles or microcapsules can occur using various reactions at a molecular level, such as interfacial polymerization procedures, complex coacervation procedures, gelation (thermal or ionic), precipitation, and so forth. Regardless of the details at a molecular level, however, the process always depends on the prior formation of droplets of suitable dimensions which can then be converted to solid or semisolid form by the above mechanisms.

For example, a preparation containing microparticles encapsulating oil soluble vitamins can be prepared by dropwise extrusion, into an aqueous calcium chloride solution, of an emulsion that consists of the oil phase dispersed in an aqueous sodium or potassium alginate solution. The liquid droplets so formed are rapidly converted to calcium alginate beads by ionic gelation when they fall into a CaCl$_2$ solution. These beads entrap and retain dispersed oil droplets. The alginate gelation procedure outlined above is not limited to immobilizing oil droplets. One can use this procedure to immobilize live plant and animal cells, bacteria, fungi, nematodes, a range of parasites, active enzymes, and intact organelles like islets of Langerhans and plant chloroplasts.

C. Thies and F. Linek, U.S. Pat. No. 4,464,317, disclosed a method whereby soluble silicate solutions containing active agents are extruded dropwise into aqueous calcium chloride solutions, thereby forming solid silicate beads or capsules loaded with active agent.

Microcapsules can also be formed by interfacial polymerization. In this technology, the material to be encapsulated is dissolved in a liquid (liquid 1) (e.g., an oil). A reactive agent is then also dissolved or suspended in liquid 1. Said reactive agent can be an acid chloride, isocyanate, epoxide, aldehyde, etc. The resulting mixture is extruded dropwise into a liquid (liquid 2) with which it is immiscible. Liquid 2 contains a coreactant for the reactant carried by liquid 1 (e.g., amines, hydroxy groups, etc.). The two coreactants meet at the liquid/liquid interface to thereby form a capsule. This polymerization process assumes the coreactants in liquids 1 and 2 are multifunctional. The encapsulation process can be carried out when liquid 1 is a water-immiscible liquid and liquid 2 is water. Liquid 2 could also be any other liquid immiscible with liquid 1. The process can also be reversed (i.e., liquid 1 is water or water-miscible and liquid 2 is water-immiscible).

The above-mentioned process can also be carried out by dropping an aqueous solution that contains reagent 1 into a second aqueous solution that contains reagent 2. The two reagents react at their mutual interface to form a capsule, as described by Pommerening, K., et al, *Biomed Biochem Acta* (1983) 42:813. Cell-loaded capsules are formed by ejecting a dispersion of cells in aqueous cellulose sulfate dropwise into a 2% aqueous solution of poly(dimethyl diallyl ammonium chloride). These two polyelectrolytes interact spontaneously to form a hydrogel capsule membrane.

In addition, particles can be formed by dropwise extrusion of a solution that gels when cooled or heated, where the solution is loaded with any active agent or other material desired. For example, when an aqueous gelatin solution is dispersed into cold, water-immiscible solvents, the gelatin solution forms gel particles. Madan, P. L., et al, *J Pharm Sci* (1978) 67:409–411, prepared spherical gelatin beads loaded with sodium salicylate solution into cold (5° C.) USP mineral oil. The product was dehydrated by acetone washing and isolated as a free-flow powder. Other materials which solidify on cooling include agar, pectin, and carrageenan. Emulsions of an oil or suspension of solid particles in solutions of these materials are encapsulated by dropwise extrusion into cold solvents.

Nakoma, M., et al, *J Pharm Pharmacol* (1979) 31:869–872, outline a procedure whereby a drug, sulfamethazole, was entrapped in an aqueous agar gel bead by thermal gelation. The beads were formed by dropwise extrusion of the aqueous drug/alginate suspension into a series of cold, water-immiscible, solvents. Beads isolated by gelation in a water-immiscible solvent were irregular (oval or coin) shaped.

Microcapsules can also be formed by complex coacervation. In this technology, originally disclosed by Green, B. K., and Schleicher, L., U.S. Pat. No. 2,800,457, gelatin and any combination of many polyanions (e.g., gum arabic, sodium alginate, carrageenan, etc.) are combined at warm temperatures (e.g., above 35° C.) to form a liquid coacervate. This liquid coacervate is in equilibrium with a dilute polymer solution called the supernatant. The two phases can be readily separated. If a water-insoluble liquid or solid is dispersed in the warm coacervate, the resulting mixture can be extruded dropwise into chilled (5° C.) supernatant phase to thereby produce gelled microcapsules. The capsules so formed can then be cross-linked or fixed by reaction with aldehydes like glutaraldehyde or with tannic acid.

Polymer precipitation is another approach to the formation of microparticles or capsules in which a dispersion or solution of active agent in a polymer/solvent solution is extruded into a nonsolvent for these materials. As an illustration of this type of process, Madan, P. L., et al, *J Pharm Pharmac* (1978) 30:65–67, extruded dropwise an aqueous solution of cellulose acetate phthalate and sodium salicylate into 5M aqueous HCl. The freshly formed capsules were uniform spheres. However, after drying, they ceased to be perfect spheres because of solvent loss due to evaporation. The dried particles did not return to spherical shape or increase in size when hydrated.

Still another approach to microparticles is described as the "hot melt" process. In this process, an active agent or a solution of active agent is emulsified or dispersed in a molten fat, wax, polymer or mixture of these ingredients. The mixture is then extruded dropwise into a cooling bath immiscible with the melt to form microcapsules or microparticles.

A different process is described in U.S. Pat. No. 4,352,883 issued to F. Lim and R. D. Moss. According to this patent, live cells or tissue are trapped in a calcium alginate gel by dropwise extrusion of a suspension of live cells or tissue in sodium or potassium alginate into dilute calcium chloride that is isotonic in nature and buffered to pH 7.2. The calcium alginate beads are then treated sequentially with a polycation and mild chelating agent (e.g., sodium citrate) to thereby yield macrocapsules with a semipermeable hydrogel membrane that encloses a liquid core that contains live cells or tissue. These capsules protect the cells and tissue from the external environment. Such capsules can be used for a variety of purposes including cell culture, drug release, chromatography support, etc.

Because the formation of microcapsules is so useful in the growth of assorted plant/animal, e.g., mammalian cells, Bellco Technology (Vineland, N.J.) markets a large bioreactor (several-liter capacity) which includes a multitip pipetting device that consists of a number of syringe needles through which cell- or tissue-loaded alginate droplets are extruded into calcium chloride solution to form calcium alginate beads. Significantly, this multitip pipetting device has no gas stream passing over the needle tips and hence has no way to control droplet (and, hence, ultimate particle size) other than by altering the size of the extrusion needle. It is not possible to produce gel beads that are less than 1.5 to 2.0 mm by this method. This bead size is too large to permit or encourage growth of live cells in the interior of the beads due to limitations of oxygen and nutrient diffusion into the interior of the beads. This is a major design limitation of the Bellco Apparatus. In addition, the Bellco apparatus is not designed to extrude small amounts of material. It is a costly and complex apparatus designed to produce bead slurry of several hundred ml to several liters. Said bead slurries are then incubated in the unique bioreactor that is an integral part of the Bellco device. The apparatus that is the subject of the instant disclosure is a stand-alone device designed to form droplets in small volume; it contains no bioreactor chamber suitable for cell culture.

A summary of various processes for formation of microcapsules is found in Thies, C., "Encyclopedia of the Polymer Science and Engineering", 2nd ed. (1987) 724–743, John Wiley & Sons, incorporated herein by reference. See also P. B. Deasy, Microencapsulation and Related Drug Processes, Marcel Dekker, Inc., New York, 1984.

In all of the foregoing instances, and indeed on almost any occasion in which microcapsules, beads, or other particulates are desired to be synthesized, uniform or controllable particle dimensions are desirable. In order to obtain uniform particles, the size of the droplets used as the core of the solidified particles must be controlled. The methods disclosed in the art—formation of emulsions, extrusion from needles without using a gas to control droplet size and other commonly accepted techniques, are not capable of regulating the particle size for small volumes or weights of material to be entrapped or encapsulated in a bead or microcapsule. The compact, simple, low-cost apparatus and method of this invention solves these problems and permits controlled droplet formation with small samples for a wide range of materials, organelles, and microorganisms.

DISCLOSURE OF THE INVENTION

The invention provides a method and apparatus for the formation of uniform size droplets which are useful in the formation of a variety of microparticulates and microcapsules, i.e., those which have diameters in the $\mu$m-mm range. The invention droplets are roughly in this arbitrarily set range and can vary from about 5 $\mu$m to 4 mm. The resulting microcapsules or microparticles are useful in a variety of contexts including growth of hybridoma and T-cells, assorted live plant cells, live plant and animal organisms, controlled release of drugs, polypeptides, pesticides, herbicides, diagnostic agent, solid supports, chromatography, and so forth.

The apparatus of the invention is a liquid dispensing device in which the liquid to be dispensed is subjected to uniform pressure and wherein the dispensed liquid is split into discrete droplets by passage of air or other gas stream across the tip of the dispenser. By virtue of this combination, the size of the droplets dispensed can be controlled and uniform size can be assured.

Thus, in one aspect, the invention is directed to a compact apparatus for forming droplets of liquid having uniform diameter which apparatus comprises a dispensing means terminating in an orifice equivalent to a 10–30 gauge needle, wherein means are provided to apply a constant pressure to a liquid in the dispensing means. The apparatus also includes a means for passing a stream of gas across the orifice so as to dislodge the droplets of uniform size in a controlled manner and thereby control droplet size. Various configurations may be envisioned to effect these features; however, all must result in a constant liquid flow pressure in combination with application of a gas stream across the orifice.

In another aspect, the invention is directed to a method to form uniform droplets using the apparatus of the invention, said uniform droplets coming from a small volume dispensing means, thereby permitting the formation of beads and microcapsules from a small amount of material.

BRIEF DESCRIPTION OF THE DRAWINGS

FIG. 1 is a front view of one preferred embodiment of the apparatus of the invention.

FIG. 2 is an enlarged view of the orifice portion of the apparatus.

FIG. 3 shows the dispensing portion of the apparatus disconnected from the pressure applying means to permit exchange of liquid to be dispensed.

MODES OF CARRYING OUT THE INVENTION

Figures 4, 5:
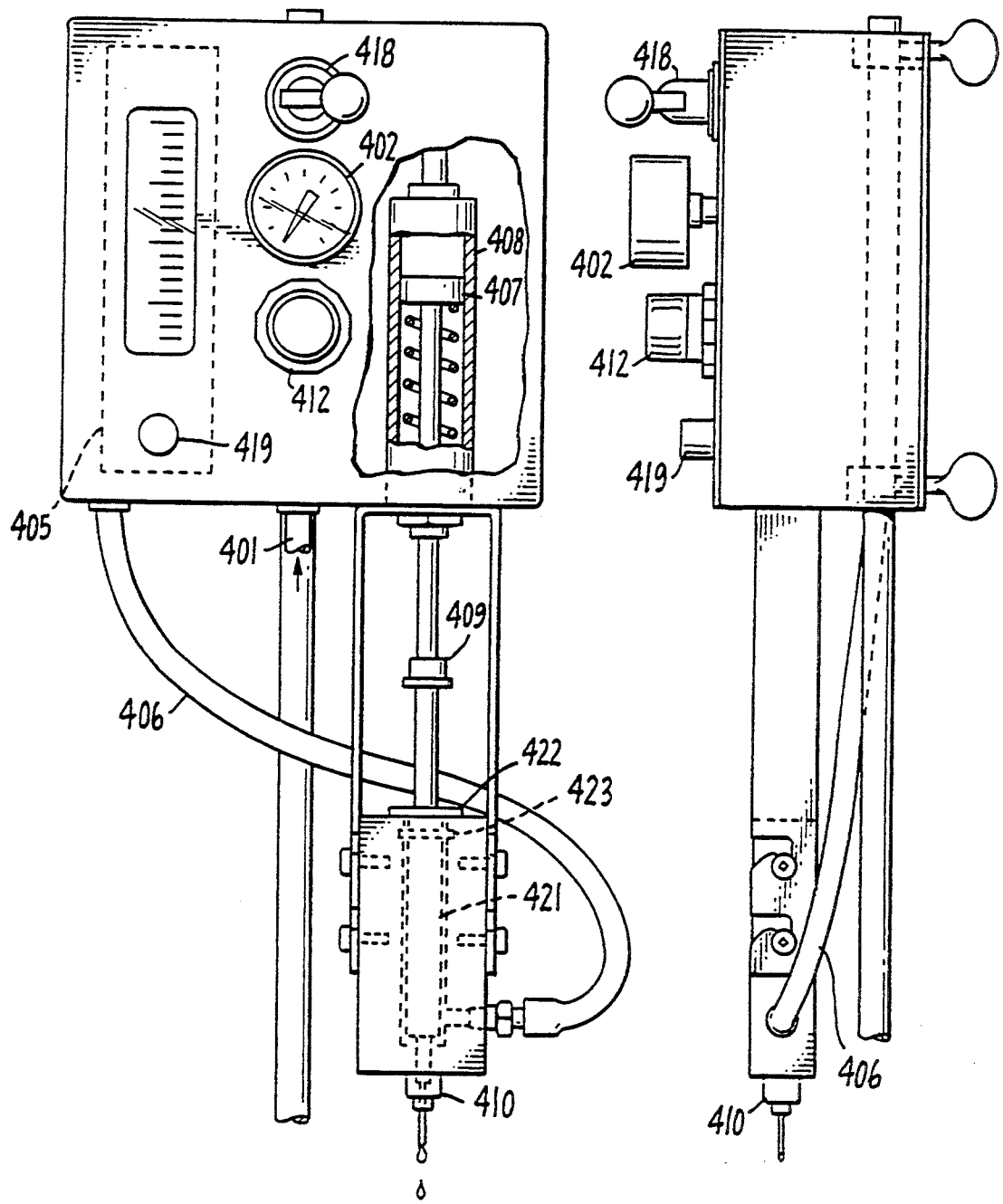
FIG. 4 is a front elevational view of a preferred embodiment of the apparatus showing the means for applying a gas stream across the orifice and the pressure-applying means, and with parts broken away to show the piston chamber for controlling the plunger.
FIG. 5 is a side elevational view of the apparatus shown in FIG. 4.

It is the principal object of the invention to provide a means to form droplets of a uniform and consistent size at the option of the operator, particularly when the operator has available a limited supply of material from which said uniform droplets are to be made. The droplets may be intended for a variety of purposes, the most common of which is the formation of microcapsules or beads which are formed when these droplets enter a medium causing them to become solid or semisolid. As described in the background section above, the droplets may contain entrapped materials such as cells, tissue, solutions or dispersions of active ingredients in liquids immiscible or miscible with the receiving liquid located at the outer surface of the droplet.

The invention provides an apparatus which permits the extrusion of droplets of uniform size. Essential features of this apparatus are a uniform pressure on the liquid which is extruded, a gas stream of regulated pressure passing over the orifice at which the droplet is formed, the flow rate of the gas stream also regulating the size of the droplet, and a small, but variable dispensing volume.

By utilizing the method and apparatus of the invention, droplets in the range of 5 μm to 4 mm can be formed, depending on the parameters regulating droplet formation and the nature of the liquid. The volume of liquid that can be extruded conveniently ranges from below 0.1 ml up to 10 or 20 ml.

More viscous liquids permit the formation of larger drops, and each liquid has inherent limitations on drop size. For an aqueous solution, for example, droplets in the range of 50 μm to 4 mm can be formed, preferably 200 μm to 4 mm.

The parameters of droplet formation which control droplet size are the diameter of the orifice of the needle, the pressure used to extrude the liquid, and the flow rate of the gas around the orifice on which the droplet formation occurs.

Thus, the greater the flow rate of the gas past the orifice, the smaller the droplets. The wider the orifice, the larger the droplets if gas flow is held constant. It is convenient to use ordinary syringe needles (beveled or blunt) ranging in size from 10 to 30 gauge. The usual pressure applied to the liquid column is, of course, dependent on the configuration of the extruding device and the size of the orifice. For orifice sizes in the range of 12–30 gauge, a pressure of 2–5 psi is often appropriate.

The rate of flow of gas past the orifice is of the order of up to 10 L/min. The workable flow rates. are relatively independent of orifice size and column pressure, although the rate utilized affects, as stated above, the resulting drop size.

The device of the invention itself is simply an extrusion device, and for most embodiments, can be designed to accommodate only small volumes. For example, a 1 ml to 20 ml syringe can be used as the dispensing part of the apparatus. For many applications, 5 to 10 ml syringes are appropriate. Standard syringes are readily available and workable. Plastic disposable syringes are of particular value. For larger numbers of droplets, the device can be scaled up to any required volume such as 100 ml or 1 liter; this would be unusual for most applications.

The formation of the droplets is intended to produce, when the droplets are suitably extruded into a receiving medium, a solid or semisolid particle. This may be a homogeneous particle or bead, or more commonly a semipermeable coating encapsulating a contained core. Typical chemistries and physical chemical conditions for forming particles of the desired size range are set forth in the background section above, and are drawn from the art. The invention is workable with any of these embodiments, and the invention contribution is to permit the production of controlled and uniform droplets for formation of the desired particles, particularly when small volumes of material are available.

Indeed, the apparatus of the invention is not limited as it does not involve parts which are controlled or driven by electricity, and thus permits the extrusion of volatile or flammable liquids without concern that electrical sparks will cause explosions or fires. As the gas flow over the orifice can be that of an inert gas if desired, so that even greater stability can be obtained. For most materials, the gas stream can simply be air; for others, it may be desirable to use helium, argon, or nitrogen. Furthermore, in many applications that are of interest to the biological community, it is important to have a portable, simple, compact extruding device that can be easily sterilized and operated in closed areas like sterile hoods. The device of this invention provides this capability.

DETAILED DESCRIPTION OF PREFERRED EMBODIMENTS

In a very simple embodiment of the invention, an aluminum tube is clamped above or partially around a mounted needle-bearing syringe loaded with the material to be extruded. A weight is placed in the tube and rests on the syringe plunger thus causing a steady pressure on the plunger and consequently upon the liquid in the tube to extrude the emulsion, slurry or suspension contained in the syringe. A stream of gas from, for example, a pressurized tank, controlled manually, blows the drops off the tip of the needle of the syringe to control drop size. For this simple embodiment, weights of 100–1,000 g are useful for a 5-10 ml syringe, depending on the viscosity of the liquid to be extruded.

The weight applied to the plunger of the syringe can of course be applied in other ways, such as through a lever arm.

In more complex and more preferred embodiments, solid weights used to drive the plunger are replaced by an air or gas driven piston. In one easily constructed embodiment, which is less preferred, the same gas stream used to blow past the orifice is used to apply pressure to the plunger. FIGS. 1–3 show this embodiment in detail.

As shown in FIG. 1, a source of gas or air 101 is pumped past a pressure regulator 102 and split into two portions at a T joint 104. One portion passes through the flow meter 105 and into the tube 106 which forces the gas to flow through a nipple 110 and past the orifice of the needle 103.

The second portion of the gas split at the T as described above is used to exert pressure on the piston shown in FIG. 1 as 107 and in FIG. 4 as 407. This portion of the gas flow enters a chamber 108 which contains the upper portion of the piston.

FIG. 2 shows the arrangement with regard to the orifice and the gas flow past it in more detail. As shown in FIG. 2, the gas passes along the side of the syringe and through a jacketed nipple through which the needle of the syringe has been passed. The nipple is secured to the base of the holder. The nipple is made of a suitable plastic such as polycarbonate, and contains screw threads so that it can be inserted onto the bottom of the base by means of these threads after the needle has protruded from the bottom of the base through a correspondingly threaded orifice in the base. An expanded drawing of the nipple is shown below as FIG. 7.

FIG. 3 shows the polycarbonate base used to hold the syringe, with the syringe in place, and the base swung away from the piston 107 which is used to apply pressure to the plunger 109. In use, the syringe is inserted into the base as shown in FIG. 2 with the needle protruding from the bottom, and the nipple, shown in FIG. 2, is then placed annularly to the needle and threaded into the base. The syringe is secure and supported on an upper finger flange and on an O-ring about one-third of the way down from the flange. This allows free suspension of the syringe and a full circumferential orifice for the air passing around the needle.

In a more preferred embodiment, separate gas supplies are used to control pressure on the plunger and gas flow past the orifice. As shown in FIG. 4, a device of the invention is mounted on a base, such as a ring stand and contains a receptacle for the syringe which is shown in place. The syringe plunger is supplied with a spring so that it automatically retracts when no pressure is applied. The air flow or gas flow enters the control metering device 405 from a T, 404, and is passed through the metering device to the side of the syringe for passage through the nipple 410. Air flow or gas flow through this gas line is controlled through the valve 419. The gas supply 401 is controlled by valve 412 and flow meter 402 and run into a closed cylinder 408 to exert pressure on the plunger 409.

FIG. 4 also shows the details of the cylinder and means for retracting the piston/plunger.

Figure 6:
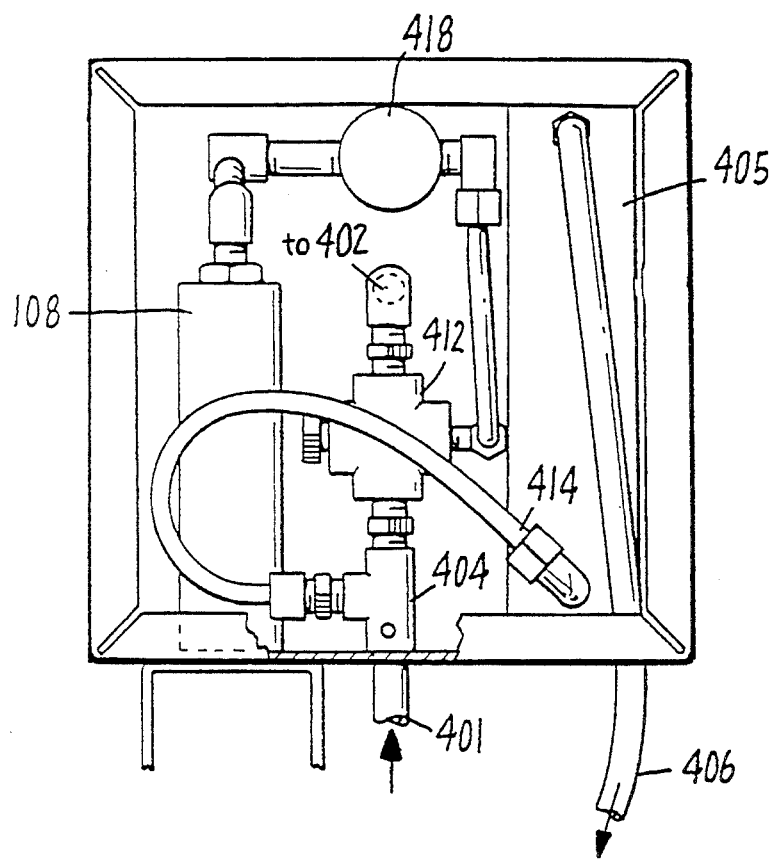
FIG. 6 is a rear elevational view of the gas supply portion of the apparatus with the rear panel removed.

These elements are seen from the side in FIG. 5 and from the back in FIG. 6. FIG. 6 shows the incoming gas line 401 wherein the flow to the orifice goes through T 404 and tube 414 into the meter 405 and out again through tube 406. Line 406 leads to the nipple on the syringe holder to provide the stream-splitting gas to form droplets.

Gas flow intended to exert pressure on the syringe is passed through valve 412 and monitored by pressure meter 402. From valve 412, the air flows through toggle valve 418 and into the piston chamber 108, where pressure is exerted on the piston 407 and transmitted to the plunger. Gas flow intended to flow past the needle is controlled by valve 419 (FIG. 4) and is exited into the nipple at the syringe barrel.

The apparatus is conveniently constructed of brass connecting parts, teflon tubing, and plastic or metal enclosures. A stainless steel outer enclosure is preferred in order to provide a chemically resistant enclosure.

Figure 7:
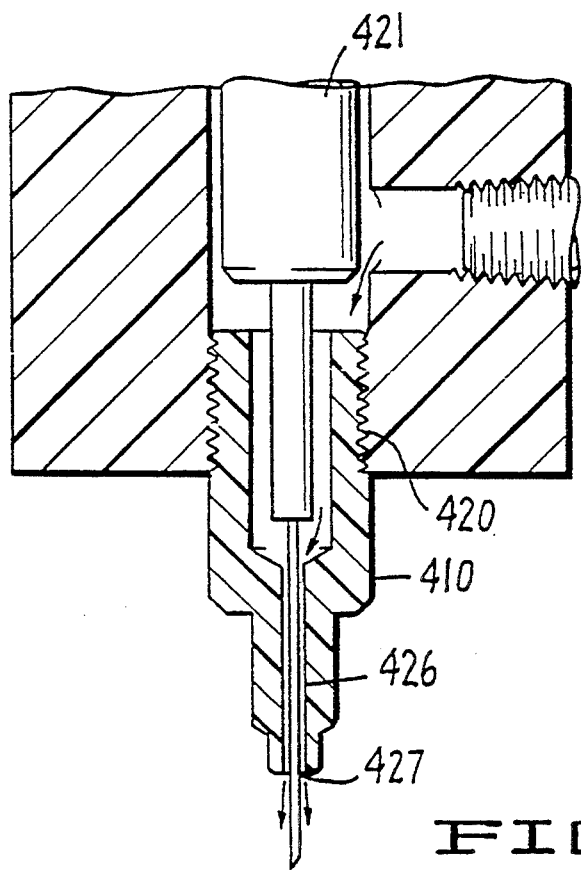
FIG. 7 shows the detail of the dispensing portion of the apparatus through which the gas stream is directed past the orifice.

FIG. 7 shows the detail of the nipple through which the syringe needle is passed. The threads 420 secure the nipple to the base. The syringe barrel 421 rests on the flange 422 (FIG. 4) and O-ring 423 (FIG. 4) the needle protrudes through the narrower channel 426 and the opening 427. The length of the nipple, length and gauge of the needle protruding through the nipple, and diameter of opening in the nipple for the needle can be varied, thereby varying droplet size obtained under a given set of operating conditions.

In operation, the apparatus is mounted on a stand, which advantageously has an off-white base so that the particles can be seen as they form. The gas pressure is attached to the apparatus as shown in FIG. 6 at 401 and an upstream main valve (not shown) is left off. An in-line filter can also be placed in the gas feed line to create sterile air or gas which can be supplied from a pressurized cylinder or an in-house pressure line.

All controls—i.e., the controls that control gas pressure on the piston and the orifice gas flow rate, are placed on zero and all valves are shut off. The loaded syringe is then inserted into the syringe holder with the nipple detached from the base. The nipple, shown in detail in FIG. 7, is then placed annularly to the syringe needle and threaded into the receiving threads in the support block.

A receiving vessel is placed in position below the needle of the syringe and the gas supply is turned on. The toggle on-off switch to the gas piston is then switched to the open position and the air valve to the piston 407 is opened to read the air pressure which first affects the plunger. The gas pressure on the plunger is kept on until the plunger extends down to the syringe barrel. The pressure at which the first drops are formed is recorded. The plunger switch is then turned to the off position causing the piston to retract and the air jet that supplies the nipple surrounding the orifice is turned on. The plunger air flow rate through the nipple is then adjusted to produce the size droplets desired. Droplet fall distance may also be adjusted by adjusting the spacing of the receiver from the tip of the needle.

By suitably adjusting the gas pressure on the plunger and flow rate of orifice gas, droplets of the desired shape and size are formed. The collection vessel then is replaced with a fresh vessel and the syringe contents are extruded into it, giving a uniform supply of drops of the desired shape.

When the desired amount of material has been extruded, the plunger switch is turned off, retracting the plunger. The air flow through the nipple is not disconnected if the syringe is to be reloaded, nor is the air pressure to the plunger. If, however, this is the end of the run, both valves are turned to off. More droplets can be formed by reloading the syringe and replacing in the syringe holder to permit additional droplets to be obtained.

It is desirable when discontinuing operations to turn off simply the main gas flow switch and plunger on-off switch so that the gas flow rates need not be reset.

EXAMPLES

The following examples are intended to illustrate but not to limit the invention.

EXAMPLE 1

Formation of Encapsulated Live Cells or Live Organisms

An alginate solution is prepared in saline, from one of several grades of alginate sold by the Kelco Division of Merck, San Diego, Calif. A preferred grade of Kelco alginate is called Improved Kelmar®, a potassium alginate. Other grades such as Kelco Gel HV® and Keltone® which are sodium alginates have also been used. All three alginates form relatively clear solutions in saline, unlike the Kelgin® grade of alginate also supplied by Kelco. Kelgin grades are not preferred, although conditions for their successful use can be defined.

The above alginates are readily dissolved with agitation in saline at room temperature. The saline must be agitated and the alginate powdered then dusted into the vortex of the agitated saline. It may take an hour or more of continuous agitation to achieve complete dissolution. Preferred alginate concentrations are 1.5 to 3.0 wt %. The latter must be used if the alginate solution is to be steam sterilized (20 min at 120° C.). Steam sterilization causes a significant decrease in alginate solution viscosity which is taken into account using a higher initial alginate concentration (e.g., 3 wt %).

The cell suspension and alginate solution are mixed. For sterilized alginate solutions, one may mix 1 volume cell suspension with 1 or 2 volumes of alginate solution at room temperature. With unsterilized alginate solutions, a 1:1 (v/v) mixture of cell suspension and 1.5 wt % alginate solution is used.

The cell suspension-alginate mixture is loaded into a 5 cc syringe. Entrapped air or air bubbles are removed. The syringe is equipped with a 23 gauge 1 inch or 25 gauge 1½ inch standard needle; the tip of the needle does not need to be ground flat and the needles can be used as normally supplied.

The device used to house the syringe in this example uses application of weight to exert pressure on the liquid in the syringe.

The loaded syringe is then placed in the plastic sleeve or holder of the microdroplet-forming device.

A 50 ml beaker is positioned (glass or plastic) beneath the syringe needle. The beaker is filled with 30 ml of 1.3 wt % $CaCl_2$ that has been buffered to pH 7.2 with 13 mM HEPES; this solution is at room temperature.

The gas pressure that drives the plunger is turned on as is the gas stream that flows past the tip of the needle. The pressure gauge for the plunger should show a gas pressure of 2 to 10 psi. The flowmeter should typically be set to give a gas flow rate up to 10 L/min. A convenient source of gas is the air outlet located on most lab benches.

Droplet extrusion is continued until the contents of the syringe have been totally extruded; at that time the piston of the apparatus is removed from the plunger of the syringe, and the syringe from the holder. At this point, the syringe (and apparatus) can be reloaded for a second extrusion, or the apparatus can be shut off.

The above operating procedure is not limited to alginate/cell suspensions. For example, a 30 volume percent emulsion of n-butyl phthalate containing fast red dye in 1.25% Methocel A-15 LV (Dow, Midland, Mich.) was prepared. This emulsion was mixed with sodium alginate solution and extruded dropwise into dilute calcium chloride to form spherical calcium alginate gel beads loaded with a dispersed oil phase. In another example, Abate E-4, an emulsifiable pesticide concentrate manufactured by American Cyanamide, Stamford, Conn., was emulsified into S-35 sodium silicate (the PQ Corporation, Valley Forge, Pa.). The resulting mixture was extruded dropwise into aqueous calcium chloride to thereby form solid, pesticide-loaded silicate beads.

We claim:

1. Apparatus for providing uniformly sized substantially spherical droplets of a desired diameter which apparatus comprises:
    a tubular chamber with a dispensing end which has, at the dispensing end an orifice of diameter corresponding to a 12–30 gauge needle, and at the other end means for effecting the extrusion of the liquid contained in the tubular chamber through said orifice while exerting a steady constant pressure on the liquid contained in the tubular chamber;
    a pressure controller for setting said steady constant pressure to a desired pressure value within a range of pressure values,
    a gas flow channel coupled to said orifice for passing a measured flow of gas past the orifice to dislodge the liquid exiting through said orifice to form said droplets of uniform size,
    and a flow controller for setting said measured flow of gas to a desired flow rate value within a range of flow rate values,
    said desired diameter being related to said desired pressure value and said desired flow rate value,
    wherein the tubular chamber is housed in an apparatus including:
    a mounted housing having a cavity supporting the tubular chamber in a vertical position;
    a gas flow inlet to the side of the cavity;
    an opening contiguous with the cavity at the bottom of the housing comprising said gas flow channel;
    a housing support for supporting said housing;
    said means for extruding comprising a piston in communication with a gas pressure chamber and positioned so as to be directly above the cavity; and
    said pressure controller comprises a gas source,
    a line coupling said gas source to said gas pressure chamber
    and a pressure adjuster for controlling the pressure exerted by said gas upon said piston.

2. Apparatus for providing uniformly sized droplets of desired diameter from a liquid which comprises:
    a tubular barrel for containing a liquid, to which is attached a narrow needle having an orifice corresponding to a 12-30 gauge needle at the tip;
    fitting inside the barrel, a retractable plunger for extrusion of the liquid through the needle past the orifice;
    a block member with a cavity, said barrel/needle/plunger being inserted into the cavity of the block member so that the needle extends through an opening at the bottom of the block;
    said block member having a gas flow inlet into a side of the cavity for flowing gas past the needle orifice; and
    a support in which said block member is mounted, said support providing a piston means above said plunger for exerting uniform pressure on the plunger when said plunger is in the vertical position by means of gas pressure applied to said piston means.

3. The apparatus of claim 2 which
    further includes a first valve member to control gas flow to the plunger;
    a second valve member to control gas flow to the orifice; and
    a means to disengage the plunger from the gas pressure.

4. The apparatus of claim 3 which further includes a third valve for shutting off gas pressure to both plunger and orifice.

5. The apparatus of claim 4 further comprising a nipple member in contact with the cavity of the block member wherein gas flows past the needle orifice via the cavity and nipple member.

6. A method of forming uniformly sized droplets of desired diameter with a liquid from an apparatus having:
    a tubular barrel for containing a liquid, to which is attached a narrow needle having an orifice corresponding to a 12-30 gauge needle at the tip;
    fitting inside the barrel, a retractable plunger for extrusion of the liquid through the needle past the orifice;
    a block member with a cavity, said barrel/needle/plunger being inserted into the cavity of the block member so that the needle extends through an opening at the bottom of the block;
    said block member having a gas flow inlet into a side of the cavity for flowing gas past the needle orifice; and a support in which said block member is mounted, said support providing a piston means above said plunger for exerting uniform pressure on the plunger when said plunger is in the vertical position by means of gas pressure applied to said piston means, said method comprising, providing a liquid in the tubular barrel, extruding the liquid from the tubular barrel through said needle orifice by exerting steady constant pressure on the liquid contained in the barrel by means of steady constant gas pressure applied to said piston means, and passing a measured flow of gas from said gas flow inlet means past said orifice to dislodge liquid exiting through said orifice to form said uniformly sized droplets.

7. The method of claim 6 wherein the liquid is a suspension containing living cells and alginate, and droplets formed are solidified to obtain microcapsules containing living cells.

* * * * *